US009150467B2

(12) United States Patent
Noe et al.

(10) Patent No.: US 9,150,467 B2
(45) Date of Patent: Oct. 6, 2015

(54) PROCESSES AND APPARATUSES FOR PREPARING AROMATIC COMPOUNDS

(71) Applicant: UOP LLC, Des Plaines, IL (US)

(72) Inventors: Jason L. Noe, Mount Prospect, IL (US); Peter Kokayeff, Naperville, IL (US)

(73) Assignee: UOP LLC, Des Plaines, IL (US)

( * ) Notice: Subject to any disclaimer, the term of this patent is extended or adjusted under 35 U.S.C. 154(b) by 280 days.

(21) Appl. No.: 13/949,104

(22) Filed: Jul. 23, 2013

(65) Prior Publication Data

US 2015/0031928 A1  Jan. 29, 2015

(51) Int. Cl.
*C07C 6/12* (2006.01)
*C10G 11/00* (2006.01)
*C10G 45/02* (2006.01)
*C07C 5/41* (2006.01)

(52) U.S. Cl.
CPC .. *C07C 5/41* (2013.01); *C07C 6/126* (2013.01)

(58) Field of Classification Search
USPC ........... 585/475, 319; 208/49, 67, 69, 70, 213
See application file for complete search history.

(56) References Cited

U.S. PATENT DOCUMENTS

| 5,599,439 A | 2/1997 | Collins et al. |
| 6,024,865 A | 2/2000 | Alexander et al. |
| 6,048,451 A | 4/2000 | Huff, Jr. et al. |
| 6,059,962 A | 5/2000 | Alexander et al. |
| 6,596,914 B2 | 7/2003 | Gore et al. |
| 7,265,252 B1 | 9/2007 | Frey et al. |
| 7,837,861 B2 | 11/2010 | Umansky et al. |
| 2013/0062254 A1 | 3/2013 | Koseoglu |
| 2013/0062255 A1 | 3/2013 | Koseoglu |

FOREIGN PATENT DOCUMENTS

| EP | 931123 A1 | 7/1999 |
| WO | 2013019527 A1 | 2/2013 |
| WO | 2013019591 A1 | 2/2013 |

*Primary Examiner* — Thuan D Dang

(57) ABSTRACT

Processes and apparatuses for preparing aromatic compounds are provided herein. In an embodiment, a process for preparing aromatic compounds includes providing a first stream that includes an aromatic component, a non-aromatic component, and a sulfur-containing component. The aromatic component and the sulfur-containing component are separated from the non-aromatic component of the first stream to form a separated aromatic stream and a raffinate stream. The separated aromatic stream includes the aromatic component and the sulfur-containing component. The raffinate stream includes the non-aromatic component. The separated aromatic stream is concurrently transalkylated and desulfurized in the presence of a catalyst that includes acid function and metal function to produce a transalkylated aromatic stream and a sulfur-containing gas stream that is separate from the transalkylated aromatic stream.

19 Claims, 2 Drawing Sheets

PROCESSES AND APPARATUSES FOR PREPARING AROMATIC COMPOUNDS

TECHNICAL FIELD

The technical field generally relates to processes and apparatuses for preparing aromatic compounds, and more particularly relates to processes and apparatuses for preparing aromatic compounds from a feed stream that includes sulfur-containing compounds.

BACKGROUND

Aromatic compounds have a multitude of uses, both as end products and as reactants for downstream processes. Methods of preparing aromatic compounds from a hydrocarbon feed are generally known in the art and include upgrading the hydrocarbon feed followed by reforming and aromatics separation. Typical upgrading techniques include hydrotreating to remove contaminants such as sulfur, nitrogen, and oxygen. After upgrading, the hydrocarbon feed is reformed in the presence of a catalyst to convert paraffins and naphthenes to a reformate that includes aromatic compounds such as xylenes, benzene, and toluene. A series of separation techniques are employed to separate the various aromatic compounds from the reformate, and numerous product streams having varying degrees of purity may be isolated for each aromatic compound in the reformate.

Hydrocarbon streams that are provided for upgrading generally include compounds that have from 6 to 10 carbon atoms, and the hydrocarbon streams may be derived from crude oil. To obtain the hydrocarbon streams including compounds that have from 6 to 10 carbon atoms, the crude oils is generally separated in a crude distillation unit, with various streams produced by the crude distillation unit including, but not limited to, various streams that primarily include compounds that have less than 6 carbon atoms and a crude bottoms stream including compounds that have greater than 10 carbon atoms. The crude bottoms stream can be cracked, such as in a fluid catalytic cracking (FCC) unit, to convert relatively high boiling point hydrocarbons (e.g., compounds that have higher numbers of carbon atoms) to lower boiling point hydrocarbons (e.g., compounds that have lower numbers of carbon atoms), resulting in a full boiling range (FBR) naphtha stream. The FBR naphtha stream generally contains paraffins, naphthenes, aromatics, unsaturated compounds, such as open-chain and cyclic olefins, dienes and cyclic hydrocarbons with olefinic side chains, with the compounds having a range of numbers of hydrocarbons. The FBR naphtha stream may be separated, such as in a naphtha splitter, to produce a C6 to C10 cracked stream that includes compounds having from 6 to 10 carbon atoms. The C6 to C10 cracked stream may be combined with the hydrocarbon stream that includes compounds that have from 6 to 10 carbon atoms from the crude distillation unit. However, the C6 to C10 cracked stream generally has a high amount of aromatic compounds that, while generally unaffected by reforming, result in unnecessarily increased loads on reforming units that are employed for reforming the hydrocarbon stream from the crude distillation unit.

While solutions have been proposed to avoid combining the C6 to C10 cracked stream with the hydrocarbon stream that includes compounds that have from 6 to 10 carbon atoms from the crude distillation unit, hydrotreating of the C6 to C10 cracked stream is still generally necessary to remove the contaminants from the C6 to C10 cracked stream. However, if the C6 to C10 cracked stream is kept separate from the hydrocarbon stream from the crude distillation unit, a separate hydrotreating unit becomes necessary to remove the contaminants from the C6 to C10 cracked stream, thereby increasing unit costs.

Accordingly, it is desirable to provide novel processes and apparatuses for preparing aromatic compounds that enable contaminants to be removed from a feed stream that includes an aromatic component, a non-aromatic component, and the contaminant. Furthermore, other desirable features and characteristics of the present invention will become apparent from the subsequent detailed description of the invention and the appended claims, taken in conjunction with the accompanying drawings and this background of the invention.

BRIEF SUMMARY

Processes and apparatuses for preparing aromatic compounds are provided herein. In an embodiment, a process for preparing aromatic compounds includes providing a first stream that includes an aromatic component, a non-aromatic component, and a sulfur-containing component. The aromatic component and the sulfur-containing component are separated from the non-aromatic component of the first stream to form a separated aromatic stream and a raffinate stream. The separated aromatic stream includes the aromatic component and the sulfur-containing component. The raffinate stream includes the non-aromatic component. The separated aromatic stream is concurrently transalkylated and desulfurized in the presence of a catalyst that includes acid function and metal function to produce a transalkylated aromatic stream and a sulfur-containing gas stream that is separate from the transalkylated aromatic stream.

In another embodiment, a process for preparing aromatic compounds includes distilling a crude carbonaceous feed that includes a sulfur-containing component to produce a crude bottoms stream and a crude intermediate stream. The crude intermediate stream includes compounds having from 6 to 10 carbon atoms. The crude bottoms stream is cracked to produce a full boiling range naphtha stream that includes the sulfur-containing component. The full boiling range naphtha stream is fractionated into a fractionation overhead stream, a fractionation bottoms stream, and a first stream. The fractionation overhead stream includes compounds having 5 or less carbon atoms. The fractionation bottoms stream includes compounds having at least 11 carbon atoms. The first stream includes the sulfur-containing component and compounds that have from 6 to 10 carbon atoms including an aromatic component and a non-aromatic component. The aromatic component and the sulfur-containing component are extracted from the non-aromatic component of the first stream to form an extraction product stream and an extraction raffinate stream. The extraction product stream includes the aromatic component and the sulfur-containing component. The extraction raffinate stream includes the non-aromatic component. The extraction product stream is concurrently transalkylated and desulfurized in the presence of a catalyst that includes acid function and metal function to produce a transalkylated aromatic stream and a sulfur-containing gas stream that is separate from the transalkylated aromatic stream.

In another embodiment, an apparatus for preparing aromatic compounds includes a crude distillation unit for distilling a crude carbonaceous feed that includes a sulfur-containing component to produce a crude bottoms stream. A fluid catalytic cracking unit is in fluid communication with the crude distillation unit for cracking the crude bottoms stream to produce a full boiling range naphtha stream. The full boiling range naphtha stream includes the sulfur-containing component. A naphtha splitter is in fluid communication with the fluid catalytic cracking unit for fractionating the full boiling range naphtha stream into a fractionation overhead stream, a fractionation bottoms stream, and a first stream. The first stream includes the sulfur-containing component and compounds that have from 6 to 10 carbon atoms including an aromatic component and a non-aromatic component. A separation unit is in fluid communication with the naphtha splitter for separating the aromatic component and the sulfur-containing component from the non-aromatic component of the first stream to form a separated aromatic stream and a raffinate stream. The separated aromatic stream includes the aromatic component and the sulfur-containing component. The raffinate stream includes the non-aromatic component. A catalytic unit is in fluid communication with the separation unit for concurrently transalkylating and desulfurizing the separated aromatic stream in the presence of a catalyst that includes acid function and metal function to produce a transalkylated aromatic stream and a sulfur-containing gas stream separate from the transalkylated aromatic stream.

BRIEF DESCRIPTION OF THE DRAWINGS

The various embodiments will hereinafter be described in conjunction with the following drawing figures, wherein like numerals denote like elements, and wherein.

DETAILED DESCRIPTION

The following detailed description is merely exemplary in nature and is not intended to limit the various embodiments or the application and uses thereof. Furthermore, there is no intention to be bound by any theory presented in the preceding background or the following detailed description.

Processes and apparatuses for preparing aromatic compounds are provided herein that enable a sulfur-containing component, and possibly other contaminants, to be removed from a feed stream that includes an aromatic component, a non-aromatic component, and the sulfur-containing component. In particular, the sulfur-containing component and the aromatic component are separated from the non-aromatic component to form a separated aromatic stream that includes the aromatic component and the sulfur-containing component. The separated aromatic stream is then concurrently transalkylated and desulfurized in the presence of a catalyst that includes acid function and metal function to produce a transalkylated aromatic stream and a sulfur-containing gas stream separate from the transalkylated aromatic stream. In this regard, the sulfur-containing component is separated from the aromatic component (and also the non-aromatic component) of the feed stream without a need for hydrotreating to separate the sulfur-containing component. Desulfurization of the separated aromatic stream, which occurs concurrently during transalkylation, is effective to separate the sulfur-containing component due to use of the catalyst that includes acid function in combination with metal function, which is resistant to deactivation and coking even in the presence of the sulfur-containing component while also converting compounds in the sulfur-containing component to sulfur-containing gas, such as $H_2S$, that can be readily separated from the aromatic component. The separated aromatic stream bypasses or avoids conventional hydrotreating and reforming stages that are traditionally employed to remove sulfur-containing species and to convert non-aromatic compounds to aromatic compounds, respectively, thereby maximizing process efficiency by reducing loads during hydrotreating and reforming.

Figure 1:
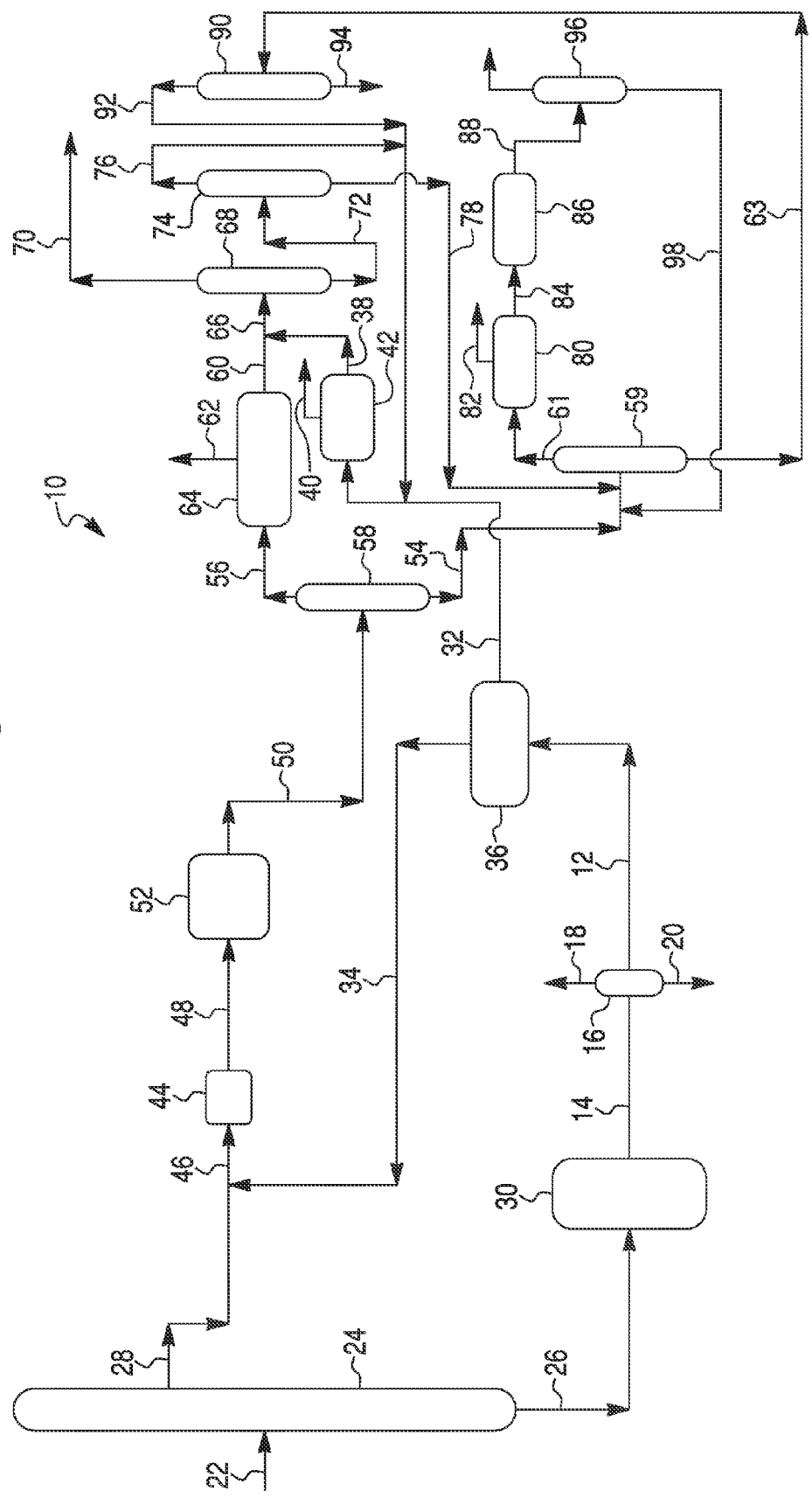
FIG. 1 is a schematic diagram of an apparatus and a method for preparing aromatic compounds in accordance with an exemplary embodiment.

An embodiment of a process for preparing aromatic compounds will now be described with reference to an exemplary apparatus 10 for producing aromatic compounds as shown in FIG. 1. In accordance with the process and as shown in FIG. 1, a first stream 12 that includes an aromatic component, a non-aromatic component, and a sulfur-containing component is provided. The sulfur-containing component, as referred to herein, includes any compounds that contain sulfur and that are present in the first stream 12. Thiophenes are examples of common sulfur-containing compounds that may be present in the first stream 12. A source of the first stream 12 is not particularly limited provided that the first stream 12 includes the aromatic component, the non-aromatic component, and the sulfur-containing component. In an embodiment and as shown in FIG. 1, the first stream 12 is obtained by fractionating a full boiling range (FBR) naphtha stream 14 that includes the sulfur-containing component in a fractionation unit 16, such as a naphtha splitter 16. The FBR naphtha stream 14 may be fractionated into a fractionation overhead stream 18, a fractionation bottoms stream 20, and the first stream 12. The fractionation overhead stream 18 generally includes compounds having 5 or less carbon atoms, the fractionation bottoms stream 20 generally includes compounds having at least 11 carbon atoms, and the first stream 12 generally includes compounds having from 6 to 10 carbon atoms and the sulfur-containing component. While the various fractionation streams may include some compounds that have more or less carbon atoms than the amounts specified within the aforementioned ranges, the various fractionation streams include a majority of compounds having the specified number of carbon atoms consistent with yields that are realized through conventional fractionation, and this applies to all references below to various streams that have compounds with a specified number of carbon atoms.

The FBR naphtha stream 14 may be obtained from any source. Examples of useful FBR naphtha feedstocks useful as the FBR naphtha stream 14 include petroleum naphthas, steam cracked naphthas, coker naphthas, fluid catalytic conversion (FCC) naphthas and blends and fractions thereof. The FBR naphtha feedstocks may be derived through fractionation of crude oil and/or heavy oil conversion units and may have end boiling points below 235° C. The FBR naphtha stream 14 generally contains paraffins, naphthenes, aromatics, and unsaturates, such as open-chain and cyclic olefins, dienes and cyclic hydrocarbons with olefinic side chains. A sulfur content of the FBR naphtha stream 14 may range from about 0.05 wt. % to about 0.7 wt. %. The processes and apparatuses described herein are particularly applicable to processing of FCC naphtha due to high aromatic content of FBR naphtha obtained through FCC processes, with recent advancements in FCC processes even further increasing aromatics yields beyond that which was previously possible.

In an embodiment and as alluded to above, the FBR naphtha stream 14 is obtained from distilling a crude carbonaceous feed 22 that includes the sulfur-containing component. In particular, the crude carbonaceous feed 22 may be distilled in a crude distillation unit 24 in accordance with conventional crude distillation processes to produce a crude bottoms stream 26 and a crude intermediate stream 28 that includes compounds having from 6 to 10 carbon atoms, among other fractionation streams that are not shown in FIG. 1. The crude bottoms stream 26 may then be cracked to produce the FBR naphtha stream 14, while the crude intermediate stream 28 does not require cracking and is provided for separate processing from the crude bottoms stream 26 as described in further detail below. An FCC unit 30 may be provided in fluid communication with the crude distillation unit 24 for cracking the crude bottoms stream 26 to produce the FBR naphtha stream 14 that includes the sulfur-containing component. The FCC process is a well-known process for the conversion of relatively high boiling point hydrocarbons to lower boiling point hydrocarbons in the heating oil or gasoline range. The FBR naphtha stream 14 may then be fractionated in the fractionation unit 16, such as the naphtha splitter 16 as described above, to provide the first stream 12. In particular, the naphtha splitter 16 may be in fluid communication with the FCC unit 30 for fractionating the FBR naphtha stream 14.

The aromatic component and the sulfur-containing component are separated from the non-aromatic component of the first stream 12 to form a separated aromatic stream 32 and a raffinate stream 34. The separated aromatic stream 32 includes the aromatic component and the sulfur-containing component, and the raffinate stream 34 includes the non-aromatic component. In an embodiment and as shown in FIG. 1, a separation unit 36 is in fluid communication with the naphtha splitter 16 for effecting separation of the aromatic component and the sulfur-containing component from the non-aromatic component of the first stream 12. Because aromatic compounds and non-aromatic compounds that have the same number of carbon atoms may have similar boiling points and may form azeotropes, the aromatic component and the sulfur-containing component may be separated from the non-aromatic component of the first stream 12 through extraction, in which case the separated aromatic stream 32 may also be referred to as an extraction product stream 32 and the raffinate stream 34 may also be referred to as an extraction raffinate stream 34. Various extraction techniques are known in the art for separating aromatics from non-aromatics. Examples of suitable extraction techniques that may be employed include, but are not limited to, azeotropic distillation, extractive distillation, and liquid/liquid solvent extraction. In a specific example, the separation unit 36 is an extraction unit 36 that operates through liquid phase extraction using an appropriate solvent to effectuate separation of the aromatic component and the sulfur-containing component from the non-aromatic component.

The separated aromatic stream 32 that includes the aromatic component and the sulfur-containing component is then concurrently transalkylated and desulfurized in the presence of a catalyst that includes acid function and metal function to produce a transalkylated aromatic stream 38 and a sulfur-containing gas stream 40 separate from the transalkylated aromatic stream 38. Referring to FIG. 1, a catalyzing unit 42 may be disposed in fluid communication with the separation unit 36 for concurrently transalkylating and desulfurizing the separated aromatic stream 32 in the presence of the catalyst that includes acid function and metal function. Transalkylation generally involves conversion of multiple alkylated aromatic compounds to primary monoalkylated aromatic compounds such as toluene and xylenes in the presence of the catalyst that includes acid function and metal function under transalkylating conditions. However, instead of employing conventional transalkylation catalysts, the catalysts that include acid function and metal function are used due to the presence of the sulfur-containing component in the transalkylated aromatic stream 38, and the catalyst that includes the acid function and metal function performs the dual function of also desulfurizing the separated aromatic stream 32 through hydrotreating. Suitable catalysts that include acid function and metal function may include a zeolite component, an acid promoted alumina, or the like. The zeolite component may be a pentasil zeolite, which include the structures of MFI, MEL, MTW, MTT and FER (IUPAC Commission on Zeolite Nomenclature), a beta zeolite, a mordenite, or an alternative structure with similar activity. The metal function may be provided, for example, by a noble metal and/or a base metal. Examples of suitable noble metals include platinum-group metals chosen from platinum, palladium, rhodium, ruthenium, osmium, and iridium. Examples of suitable base metals include those chosen from rhenium, tin, germanium, lead, cobalt, nickel, molybdenum, indium, gallium, zinc, uranium, dysprosium, thallium, and mixtures thereof. The base metal may be combined with another base metal, or with a noble metal. The metal component may be present in the metallic, oxide, sulfide or other catalytically active form. Suitable metal amounts in the catalyst that includes acid function and metal function may be from about 0.01 to about 10 weight %, such as from about 0.1 to about 3 weight %, or such as from about 0.1 to about 1 weight %. Suitable zeolite amounts in the catalyst that includes acid function and metal function may be from about 1 to about 99 weight %, such as from about 10 to about 90 weight %, or such as from about 25 to about 75 weight %. The balance of the catalyst that includes acid function and metal function may be an inorganic oxide binder. The catalysts that include acid function and metal function may be employed under conventional transalkylation conditions and further under conditions that promote hydrotreating of the sulfur compounds.

Because the catalyst that includes acid function and metal function is used, prior removal of the sulfur-containing component at an upstream stage is unnecessary. Whereas hydrotreating may conventionally be used to remove sulfur-containing species from hydrocarbon streams, the separated aromatic stream 32 may be concurrently transalkylated and desulfurized in the absence of prior hydrotreating of the first stream 12 at any stage between the fractionation unit 16 and the catalyzing unit 42, and further in the absence of prior hydrotreating of any source of the first stream 12 such as the crude carbonaceous feed 22 or any stream derived therefrom to produce the separated aromatic stream 32 that is concurrently transalkylated and desulfurized. In this regard, process efficiency is maximized while minimizing associated costs of an extra hydrotreating unit.

As set forth above, in an embodiment where the crude carbonaceous feed 22 is distilled in the crude distillation unit 24 to produce the crude intermediate stream 28, the crude intermediate stream 28 may be further processed separate from the crude bottoms stream 26. For example, the crude intermediate stream 28 may be hydrotreated for purposes of removing sulfur species that may be present in the crude intermediate stream 28. In an embodiment and as shown in FIG. 1, a hydrotreating unit 44 is in fluid communication with the crude distillation unit 24 for receiving the crude intermediate stream 28 and for hydrotreating the crude intermediate stream 28. The crude intermediate stream 28 generally includes compounds that have from 6 to 10 carbon atoms. Because the raffinate stream 34 that includes the non-aromatic component also generally includes compounds that have from 6 to 10 carbon atoms, the raffinate stream 34 may be combined with the crude intermediate stream 28 prior to hydrotreating to produce a combined C6 to C10 stream 46 for purposes of concurrently upgrading the compounds in the raffinate stream 34 and the crude intermediate stream 28.

Hydrotreating may be conducted through conventional techniques to produce a hydrotreated stream 48.

After hydrotreating, the hydrotreated stream 48 is catalytically reformed in the presence of a platinum- and/or rhenium-containing catalyst to produce a reformate stream 50 that includes paraffins and an aromatic conversion component. In an embodiment and as shown in FIG. 1, a reforming unit 52 is in fluid communication with the hydrotreating unit 44 for receiving the hydrotreated stream 48 and for reforming the hydrotreated stream 48 to produce a reformate stream 50. To reform the hydrotreated stream 48, the hydrotreated stream 48 may be mixed with hydrogen, followed by contacting the resulting stream with the platinum- and/or rhenium-containing catalyst to convert paraffins and naphthenes in the hydrotreated stream 48 to aromatic compounds through dehydrogenation and cyclization. Reforming may be conducted under conventional conditions, and conventional platinum- and/or rhenium-containing catalysts may be employed.

Aromatic compounds that are produced through reforming generally include benzene, toluene, and xylenes, all of which may be useful end products for various applications. In accordance with an embodiment, the reformate stream 50 is fractionated to produce a reformate bottoms stream 54 that includes compounds having at least 7 carbon atoms (e.g., xylenes and compounds that have more than 7 carbon atoms) and a reformate overhead stream 56 that includes compounds having less than 7 carbon atoms (e.g., benzene, toluene, and any hydrocarbons having less than 6 carbon atoms that remain in the reformate stream 50 after reforming). For example, a reformate splitter 58 may be in fluid communication with the reforming unit 52 for receiving the reformate stream 50 and for fractionating the reformate stream 50.

Aromatic compounds may be separated from the reformate overhead stream 56 to produce a reformate aromatic stream 60 and a reformate raffinate stream 62, while the reformate bottoms stream 54 may be further processed for xylene recovery. In particular, in an embodiment and as shown in FIG. 1, a xylene column 59 may be in fluid communication with the reformate splitter 58 for receiving the reformate bottoms stream 54 and for fractionating the reformate bottoms stream 54 into a xylene fractionation overhead stream 61 that includes xylenes and a xylene fractionation bottoms stream 63 that includes compounds having at least 9 carbon atoms. Like the first stream 12, the reformate overhead stream 56 includes aromatic compounds and non-aromatic compounds that may be difficult to separate through conventional fractionation due to similar boiling points. As such, the extraction techniques described above may be employed to effectuate separation of the reformate overhead stream 56. In an embodiment and as shown in FIG. 1, a second separation unit 64 is in fluid communication with the reformate splitter 58 for receiving the reformate overhead stream 56. In a specific example, the second separation unit 64 is a sulfolane extraction unit 64 that operates through liquid phase extraction using sulfolane as a solvent to effectuate separation of the aromatic compounds from the non-aromatic compounds in the reformate overhead stream 56.

The reformate aromatic stream 60 and the transalkylated aromatic stream 38 both include aromatic compounds that may be further separated to recover the various aromatic compounds through conventional techniques to yield separate benzene, xylene, and, if desired, toluene fractions. Alternatively, toluene may be further transalkylated to yield additional benzene and xylenes therefrom. In an embodiment and as shown in FIG. 1, the reformate aromatic stream 60 and the transalkylated aromatic stream 38 from the catalyzing unit 42 are combined to form a combined aromatics stream 66, which may then be subject to conventional aromatics separation. In particular, in an embodiment and as shown in FIG. 1, a benzene column 68 is in fluid communication with the catalyzing unit 42 and with the second separation unit 64 for receiving the combined aromatics stream 66. The combined aromatics stream 66 is fractionated into a benzene fraction 70 and a C7+ bottoms stream 72 within the benzene column 68. The benzene fraction 70 includes primarily benzene, e.g., at least 50 weight % benzene, although higher purity benzene is generally obtained in the benzene fraction 70. The C7+ bottoms stream 72 primarily includes compounds that have at least 7 carbon atoms, e.g., at least 50 weight % of compounds that have at least 7 carbon atoms. The benzene fraction 70 may be taken as a product stream or used in other industrial processes. A toluene column 74 is in fluid communication with the benzene column 68 for receiving the C7+ bottoms stream 72, and the C7+ bottoms stream 72 is fractionated within the toluene column 74 into a toluene fraction 76 and a C8+ fraction 78 that includes compounds having at least 8 carbon atoms such as, for example, xylenes and C9 and C10+ aromatic compounds. In an embodiment and as shown in FIG. 1, the toluene fraction 76 is returned to the catalyzing unit 42 for conversion into benzene and xylenes through disproportionation and transalkylation, although it is to be appreciated that in other embodiments the toluene fraction 76 may be taken as a product stream or used in other industrial processes. The C8+ fraction 78 may be combined with the reformate bottoms stream 54 to be further processed for xylene recovery. The xylene fractionation bottoms stream 63 may be further fractionated in an A9/A10 fractionation column 90 that is in fluid communication with the xylene column 59. In particular, the xylene fractionation bottoms stream 63 may be fractionated into an A9/A10 fraction 92 that primarily includes compounds having 9 and 10 carbon atoms, e.g., at least 50 weight % of compounds that have 9 or 10 carbon atoms, and an A11+ fraction 94 that primarily includes compounds having at least 11 carbon atoms, e.g., at least 50 weight % of compounds that have at least 11 carbon atoms. The A9/A10 fraction 92 may be combined with the toluene fraction 76 and, in the embodiment shown in FIG. 1, the combined toluene fraction 76 and the A9/A10 fraction 92 are transalkylated as described above.

The xylene fractionation overhead stream 61 generally includes various xylene isomers, such as para-xylene, meta-xylene, and/or ortho-xylene, and the various isomers in the xylene fractionation overhead stream 61 may be further processed for xylene isomer separation. Para-xylene is generally a more commercially valuable xylene isomer than other xylene isomers and, thus, is generally separated from the other xylene isomers through conventional separation techniques. For example, in an embodiment and as shown in FIG. 1, an adsorption unit 80 is in fluid communication with the xylene column 59 for receiving the xylene fractionation overhead stream 61 and for separating the xylene fractionation overhead stream 61 through adsorption/desorption to produce a para-xylene stream 82 and a xylene raffinate stream 84. The xylene raffinate stream 84 may be further isomerized through conventional techniques in an isomerization unit 86 that is in fluid communication with the adsorption unit 80, thereby converting some of the meta- and ortho-xylenes to para-xylenes and producing a converted xylene stream 88. The converted xylene stream 88 may be fractionated in a second xylene fractionation unit 96 to recover xylenes in a second xylene bottoms stream 98, which may be combined with the reformate bottoms stream 54 to be further processed for xylene recovery.

Figure 2:
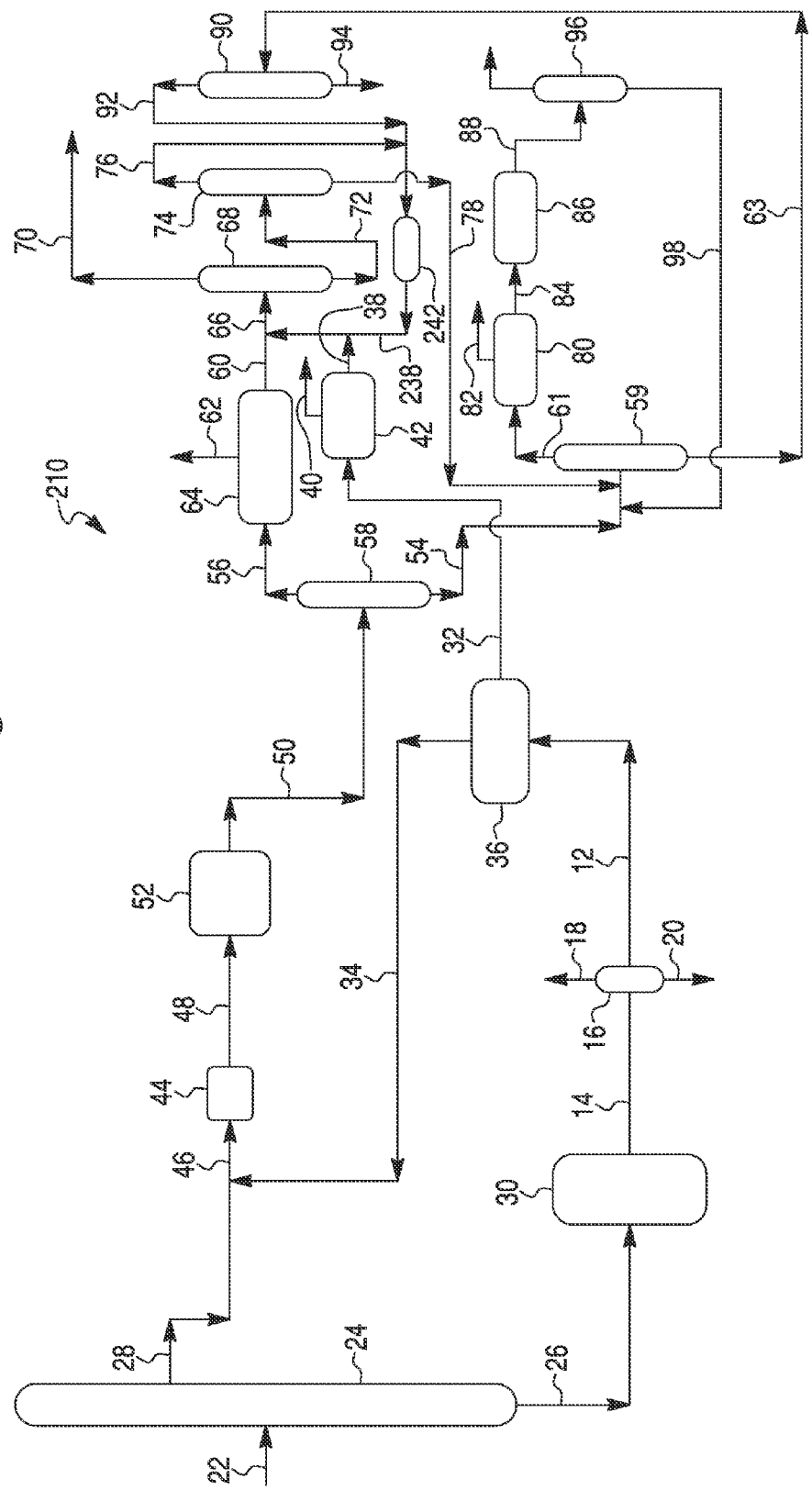
FIG. 2 is a schematic diagram of an apparatus and a method for preparing aromatic compounds in accordance with another exemplary embodiment.

Another embodiment of a process and apparatus 210 for preparing aromatic compounds is shown in FIG. 2. The apparatus 210 of FIG. 2 is similar to the apparatus 10 of FIG. 1, except that a second catalyzing unit 242 is provided in addition to the catalyzing unit 42 that receives the separated aromatic stream 32. The second catalyzing unit 242 is in fluid communication with the toluene column 74 and with the A9/A10 fractionation column 90 for transalkylating the toluene fraction 76 and the A9/A10 fraction 92 separate from the separated aromatic stream 32 to produce a second transalkylated aromatic stream 238. The second transalkylated aromatic stream 238 may be combined with the transalkylated aromatic stream 38 produced by the catalyzing unit 42. In this embodiment, the catalyzing unit 42 and the second catalyzing unit 242 are used because the concentrations of multiple alkylated aromatic compounds in the respective separated aromatic stream 32 and the toluene fraction 76 and the A9/A10 fraction 92 are different, with the separated aromatic stream 32 including a higher content of xylenes that do not require transalkylation and with the presence of xylenes in the separated aromatic stream 32 potentially depressing reactivity of the catalyst that includes acid function and metal function in the catalyzing unit 42. As such, the second catalyzing unit 242 may more efficiently process the toluene fraction 76 and the A9/A10 fraction 92 as compared to the scheme in the apparatus 10 of FIG. 1 in which the toluene fraction 76 and the A9/A10 fraction 92 are transalkylated along with the separated aromatic stream 32.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A process for preparing aromatic compounds, the process comprising the steps of:
    providing a first stream comprising an aromatic component, a non-aromatic component, and a sulfur-containing component;
    separating the aromatic component and the sulfur-containing component from the non-aromatic component of the first stream to form a separated aromatic stream comprising the aromatic component and the sulfur-containing component and a raffinate stream comprising the non-aromatic component;
    feeding the separated aromatic stream comprising the aromatic component and the sulfur-containing component to a reactor containing a catalyst containing an acid function selected from the group consisting of MFI, MEL, MTW, FER, beta zeolite, mordenite, and acid promoted alumina, and a metal function selected from the group consisting of platinum, palladium, rhodium, ruthenium, osmium, iridium, rhenium, tin, germanium, lead, cobalt, nickel, molybdenum, indium, gallium, zinc, uranium, dysprosium, thallium, and mixtures thereof to transalkylate the aromatic component to a transalkylated aromatic stream, concurrently desulfurizing by converting the sulfur-containing component to a sulfur-containing gas stream separate from the transalkylated aromatic stream.

2. The process of claim 1, wherein providing the first stream comprises fractionating a full boiling range naphtha stream comprising the sulfur-containing component into a fractionation overhead stream comprising compounds having 5 or less carbon atoms, a fractionation bottoms stream comprising compounds having at least 11 carbon atoms, and the first stream comprising compounds having from 6 to 10 carbon atoms and the sulfur-containing component.

3. The process of claim 2, further comprising cracking a crude bottoms stream from crude distillation to produce the full boiling range naphtha stream.

4. The process of claim 1, further comprising hydrotreating the raffinate stream comprising the non-aromatic component to produce a hydrotreated stream.

5. The process of claim 4, further comprising catalytically reforming the hydrotreated stream in the presence of a platinum- and/or rhenium-containing catalyst to produce a reformate stream comprising normal paraffins and an aromatic conversion component.

6. The process of claim 5, further comprising fractionating the reformate stream to produce a reformate bottoms stream comprising compounds having at least 7 carbon atoms and a reformate overhead stream comprising compounds having less than 7 carbon atoms.

7. The process of claim 6, further comprising recovering xylenes from the reformate bottoms stream.

8. The process of claim 7, wherein recovering xylenes from the reformate bottoms stream comprises fractionating the reformate bottoms stream into a xylene fractionation overhead stream comprising xylenes and a xylene fractionation bottoms stream comprising compounds having at least 9 carbon atoms.

9. The process of claim 8, further comprising further fractionating the xylene fractionation bottoms stream into an A9/A10 fraction comprising compounds having 9 and 10 carbon atoms and an A11+ fraction comprising compounds having at least 11 carbon atoms.

10. The process of claim 9, further comprising fractionating the combined aromatics stream into a benzene fraction, a toluene fraction, and a C8+ comprising compounds having at least 8 carbon atoms, and wherein the toluene fraction and the A9/A10 fraction are further transalkylated.

11. The process of claim 10, where transalkylating the toluene fraction and the A9/A10 fraction is conducted separately from concurrent transalkylation and desulfurization of the separated aromatic stream.

12. The process of claim 6, further comprising separating aromatic compounds from the reformate overhead stream to produce a reformate aromatic stream and a reformate raffinate stream.

13. The process of claim 12, further comprising combining the reformate aromatic stream and the transalkylated aromatic stream from concurrent transalkylation and desulfurization of the separated aromatic stream to form a combined aromatics stream.

14. The process of claim 13, further comprising fractionating the combined aromatics stream into a benzene fraction, a toluene fraction, and a C8+ fraction comprising compounds having at least 8 carbon atoms.

15. The process of claim 1, wherein separating the aromatic component and the sulfur-containing component from the non-aromatic component of the first stream comprises extracting the aromatic component and the sulfur-containing component.

16. The process of claim 1, wherein separating the aromatic component and the sulfur-containing component from the non-aromatic component of the first stream comprises separating the aromatic component and the sulfur-containing component from the non-aromatic component of the first stream in the absence of prior hydrotreating of the first stream.

17. A process for preparing aromatic compounds, the process comprising the steps of:
   distilling a crude carbonaceous feed comprising a sulfur-containing component to produce a crude bottoms stream and a crude intermediate stream comprising compounds having from 6 to 10 carbon atoms;
   cracking the crude bottoms stream to produce a full boiling range naphtha stream comprising the sulfur-containing component;
   fractionating the full boiling range naphtha stream into a fractionation overhead stream comprising compounds having 5 or less carbon atoms, a fractionation bottoms stream comprising compounds having at least 11 carbon atoms, and a first stream comprising the sulfur-containing component and compounds having from 6 to 10 carbon atoms including an aromatic component and a non-aromatic component;
   extracting the aromatic component and the sulfur-containing component from the non-aromatic component of the first stream to form an extraction product stream comprising the aromatic component and the sulfur-containing component and an extraction raffinate stream comprising the non-aromatic component;
   feeding the separated aromatic stream comprising the aromatic component and the sulfur-containing component to a reactor containing a catalyst containing an acid function selected from the group consisting of MFI, MEL, MTW, FER, beta zeolite, mordenite, and acid promoted alumina, and a metal function selected from the group consisting of platinum, palladium, rhodium, ruthenium, osmium, iridium, rhenium, tin, germanium, lead, cobalt, nickel, molybdenum, indium, gallium, zinc, uranium, dysprosium, thallium, and mixtures thereof to transalkylate the aromatic component to a transalkylated aromatic stream, concurrently desulfurizing by converting the sulfur-containing component to a sulfur-containing gas stream separate from the transalkylated aromatic stream.

18. The process of claim 17, further comprising hydrotreating the extraction raffinate stream comprising the non-aromatic component to produce a hydrotreated stream.

19. The process of claim 18, further comprising combining the extraction raffinate stream and the crude intermediate stream prior to hydrotreating to produce a combined C6 to C10 stream, and wherein hydrotreating the extraction raffinate stream comprises hydrotreating the combined C6 to C10 stream.

\* \* \* \* \*